US008976936B1

(12) United States Patent
Alzaidi et al.

(10) Patent No.: US 8,976,936 B1
(45) Date of Patent: Mar. 10, 2015

(54) COLLIMATOR FOR BACKSCATTERED RADIATION IMAGING AND METHOD OF USING THE SAME

(71) Applicant: King Abdulaziz University, Jeddah (SA)

(72) Inventors: Samir Abdul-Majid Alzaidi, Jeddah (SA); Ahmed S. Balamesh, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 14/285,422

(22) Filed: May 22, 2014

(51) Int. Cl.
*G21K 1/02* (2006.01)
*G01N 23/203* (2006.01)

(52) U.S. Cl.
CPC ............... *G21K 1/02* (2013.01); *G01N 23/203* (2013.01)
USPC .......................................................... 378/149

(58) Field of Classification Search
USPC ............................................ 378/147–155, 57
See application file for complete search history.

(56) References Cited

U.S. PATENT DOCUMENTS

| 3,197,638 | A | * | 7/1965 | Sinclair ........................... 378/86 |
| 4,580,053 | A | | 4/1986 | Snyder |
| 4,651,002 | A | * | 3/1987 | Anno ......................... 250/336.1 |
| 5,195,117 | A | | 3/1993 | Ong |
| 5,559,851 | A | * | 9/1996 | Schmitt .......................... 378/155 |
| 5,970,116 | A | | 10/1999 | Dueholm et al. |
| 6,252,930 | B1 | | 6/2001 | MacKenzie |
| 6,421,418 | B1 | | 7/2002 | Schulte |
| 6,895,074 | B2 | | 5/2005 | Benedetti |
| 2003/0235272 | A1 | * | 12/2003 | Appleby et al. ............... 378/147 |
| 2007/0025518 | A1 | * | 2/2007 | Levene et al. .................. 378/149 |
| 2009/0175412 | A1 | * | 7/2009 | Grodzins et al. ................ 378/57 |

FOREIGN PATENT DOCUMENTS

| WO | WO 9322661 A1 | 11/1993 |
| WO | WO 9733141 A1 | 9/1997 |
| WO | WO 9914581 A1 | 3/1999 |

* cited by examiner

*Primary Examiner* — Irakli Kiknadze
(74) *Attorney, Agent, or Firm* — Richard C Litman

(57) ABSTRACT

The collimator for backscattered radiation imaging has a plurality of parallel, arrayed passages formed therethrough. The collimator is positioned in front of a radiographic imaging device, such as a radiographic plate, radiographic film or the like, such that the plurality of parallel, arrayed passages are positioned orthogonal to a plane of the radiographic imaging device. An object, such as a wall of an insulated pipe, for example, is then exposed to gamma or X-ray radiation, and image exposures are made on the radiographic imaging device of backscattered radiation from the wall of the insulated pipe or other object. The collimator is shifted in between each of the exposures. The collimator may have a parallelepiped body, or, alternatively, may have a cylindrical body. The parallelepiped collimator is shifted linearly in front of the radiographic imaging device, and the cylindrical collimator is rotated in front of the radiographic imaging device.

2 Claims, 7 Drawing Sheets

COLLIMATOR FOR BACKSCATTERED RADIATION IMAGING AND METHOD OF USING THE SAME

BACKGROUND OF THE INVENTION

1. Field of the Invention

The present invention relates to gamma and X-ray backscatter imaging, and particularly to a collimator used in nondestructive testing, medical imaging, pipe inspection, general imaging and inspection and the like.

2. Description of the Related Art

Large insulated pipes are often found in gas producing plants for carrying both liquids and gas. The insulation around the pipes is necessary for maintaining relatively low liquid temperatures. Such insulated pipes are also commonly found in electric power plants, where the insulation is used to maintain a relatively high fluid temperature. The insulation layer on the pipes in these plants, as well as in various other industrial applications, is typically at least several centimeters thick, thus making it extremely difficult to inspect the pipe bodies for corrosion. Plant production must be stopped for interior visual inspection of the pipe walls, and removal of the outer insulation for exterior visual inspection not only requires a great deal of time and expense, but can be detrimental to the pipe itself. Ice forms on the exposed pipe surface for low temperature applications, accompanied by potentially dangerous increases of pressure in the interior, and heat is lost in high temperature applications. Additionally, such visual inspections of the pipe exterior will not indicate corrosion formed on the interior of the pipe. As noted above, conventional interior inspection would require a shutdown of the plant processes.

Although direct radiography allows for inspection of such pipes without the removal of the insulation layer, direct radiography has a number of drawbacks. As illustrated in FIG. 2, in conventional direct radiographic inspection, a radiation source 100 is positioned on one side of the object under inspection and radiographic film or an image plate is positioned opposite the source 100. In the specific application of insulated pipe inspection, a radiation source 100 emits radiation 102, which may be X-rays, gamma rays or the like, which pass through an insulated pipe, formed from a conventional pipe 106 carrying some sort of fluid 112 and surrounded by an outer annular insulation layer 104. A radiographic film or image plate 110 is placed beneath the pipe 106 for imaging corrosion 108 formed on the pipe 106.

The attenuation of X-ray and gamma ray radiation is very high in large bodies, such as in the exemplary insulated pipe of FIG. 2. If the object is very large, not enough radiation reaches the film or image plate 110 due to attenuation in the fluid 112 and in the metal wall (typically iron or iron-based materials) of the pipe 106. Additionally, as illustrated in FIG. 2, a relatively wide beam must be used, allowing for inspection of all sides of the pipe, which is often not possible for very large pipes or tanks. If a linear accelerator is used as the radiation source, such a wide beam is often impossible to produce. Further, due to the use of the single source, all sides of the pipe are imaged at the same time. This often creates confusion about the actual location of corrosion 108, since the image produced on the plate 110 is two-dimensional.

Gamma ray backscattering and X-ray fluorescence are known techniques for determining metal thickness, such as in measuring the thickness of corroded portions of metal bodies. In backscattered radiation imaging, a gamma ray beam is projected incident on the wall of the pipe. Its energy can be selected to be great enough that attenuation in the insulator is insignificant. As gamma rays or X-rays penetrate the pipe, the radiation undergoes attenuation, the radiation intensity decreasing exponentially with wall thickness. The magnitude of attenuation depends on the energy of the incident radiation and the nature of the material. Backscattering takes place from within layers of the wall by Compton interactions. The backscattered radiation undergoes higher attenuation in its path back to the detector or the film, since its energy is lower than that of the primary incident radiation. The radiation will, therefore, undergo double attenuation.

In X-ray fluorescence (XRF) imaging, the radiation incident interacts with the pipe material, followed by emission of XRF radiation. This type of X-ray is characteristic of wall materials. Most pipes and vessels of interest have walls made from iron or iron-based materials. The emitted X-rays have relatively small energies, typically around 7 keV. Additional detectors having high sensitivity for low energy radiation may be used if the first detector is not sensitive enough. It is generally preferable to use a radiation source that emits low energy in order to have a high level of reaction with the object materials. Because of the low energy of the XRF radiation, it is emitted from the surface of the object wall. Thus, it can image the outer surface of the object. This makes XRF desirable for insulated pipe inspection, since corrosion usually takes place in the outer surface of the pipe due to moisture trapped under the insulating layer.

In FIG. 3, a radioactive source 100 emits one or a few well-defined gamma rays. The radiation 102, which is incident on the pipe wall 106 (and passes through insulating layer 104), is collimated by a collimator 114. A portion of incident radiation 102 will backscatter due to Compton interactions, and a portion will also produce XRF radiation. The backscattered radiation 124 is measured by a gamma ray detector 118 (typically including a spectrometer, such as a NaI (Tl) scintillation detector), while the XRF radiation 120 is measured by a low energy X-ray detector 116, such as a CdTe, Si(Li) or HgI$_2$ detector.

Backscattered radiation, measured at a fixed angle θ, and the XRF each give defined peaks when measured with energy analyzers, such as conventional multichannel analyzers. Counting windows can be selected to measure backscattered radiation peaks and XRF radiation. Single detectors, as illustrated in FIG. 3, are limited in their functionality, due to limitations in positioning, fixed degrees of angular measurement, and limited views of only portions of a pipe under inspection. More importantly, backscattered gamma radiation is not mono-directional. The backscattered rays are scattered in all directions, thus creating a fuzzy image when the radiation reaches the film or imaging plate. Thus, in order to select a parallel beam from the scattered radiation, it would be desirable to have a suitable collimator to use with the scattered radiation.

Several different approaches have been used for backscatter imaging. In point by point imaging, a narrow collimated beam is focused on a point on the surface of the object. Scattered radiation at a fixed angle is measured by a single detector, and the object and detector are moved in two dimensions. The scattered radiation from each point of the surface is used to construct an image. This type of imaging usually takes a relatively long time, though using a larger size detector or a stronger source can increase sensitivity and speed. In line by line imaging, a slit beam is incident on the surface and scattered radiation is measured by a linear detector array. In such a system, a large number of detectors is usually used. In plane by plane imaging a wide beam is incident on the object surface, and the scattered radiation is allowed to pass through a pinhole in an absorber and then fall onto a two dimensional image plate. In this arrangement, part of the incident radiation is obscured by the absorber itself. For applications such as corrosion measurements, which usually use high energy radiation, a thick absorber needs to be used in order to stop the radiation. Thus, a beam passing through a thick plate will not be sharp and image quality will be affected. Moreover, this arrangement would not provide time savings over point by point imaging because a long time is needed to collect enough radiation to form the image.

A flying spot system has also been used, in which a stationary horizontal slot collimator beam is intercepted by a rotating disc collimator that has radial slots. At the intersection of the line slot beam and the holes slots on the rotating disc, a narrow beam is defined. The system was successfully used for surface imaging of large objects but cannot be used for field imaging, such as nondestructive imaging, because it is relatively bulky, expensive and requires a large power supply. It also uses a low energy X-ray machine that cannot image thickness variations in thick wall objects, such as imaging corrosion in thick wall pipes.

Thus, a collimator for backscattered radiation imaging and a method of using the same solving the aforementioned problems is desired.

SUMMARY OF THE INVENTION

In order to inspect an object, such as an insulated pipe, for example, a collimator is provided having a plurality of parallel, arrayed passages formed therethrough. The collimator is positioned in front of a radiographic imaging device, such as a radiographic plate, radiographic film or the like, such that the plurality of parallel, arrayed passages are positioned orthogonal to a plane of the radiographic imaging device. A wall of the insulated pipe (or other object to be inspected) is then exposed to gamma or X-ray radiation, and multiple (or continuous) image exposures are made on the radiographic imaging plate with backscattered gamma radiation from the wall of the insulated pipe or other object to be inspected. The collimator is incrementally shifted between each of the exposures. It should be understood that the collimator may also be shifted continuously with continuous exposure.

In one embodiment, the collimator is formed as a radiation-shielding body with a substantially parallelepiped contour. The radiation-shielding body has solid, longitudinally opposed top and bottom walls, solid, laterally opposed sidewalls, and transversely opposed front and rear walls. The plurality of passages are transversely formed through the radiation-shielding body. Each passage extends between the front and rear walls and has a square cross-section.

In an alternative embodiment, the collimator is also formed as a radiation-shielding body, but is substantially cylindrical. The radiation-shielding body has a solid side wall and axially opposed front and rear walls. The plurality of passages are axially formed through the radiation-shielding body. Each passage extends between the front and rear walls and has a square cross-section.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
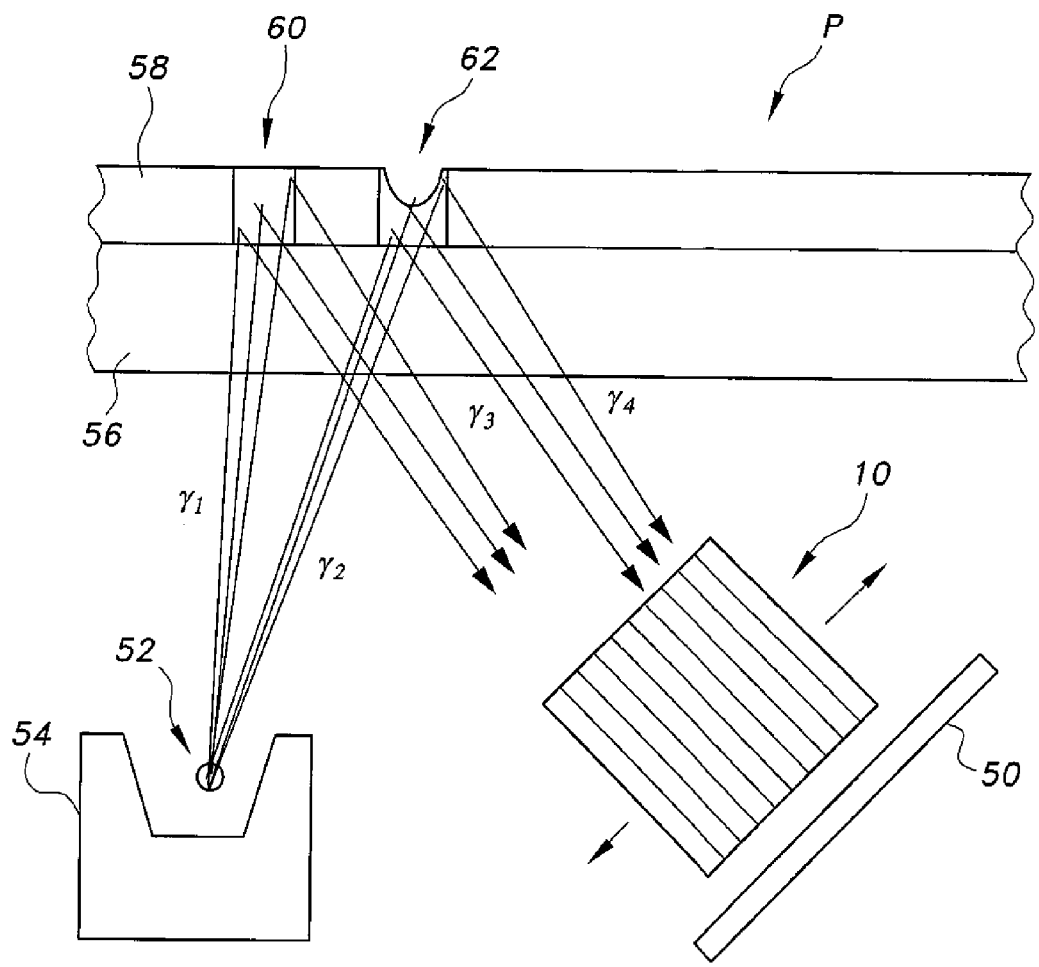
FIG. 1 is a diagram illustrating use of a collimator for backscattered radiation imaging according to the present invention.
Figure 2:
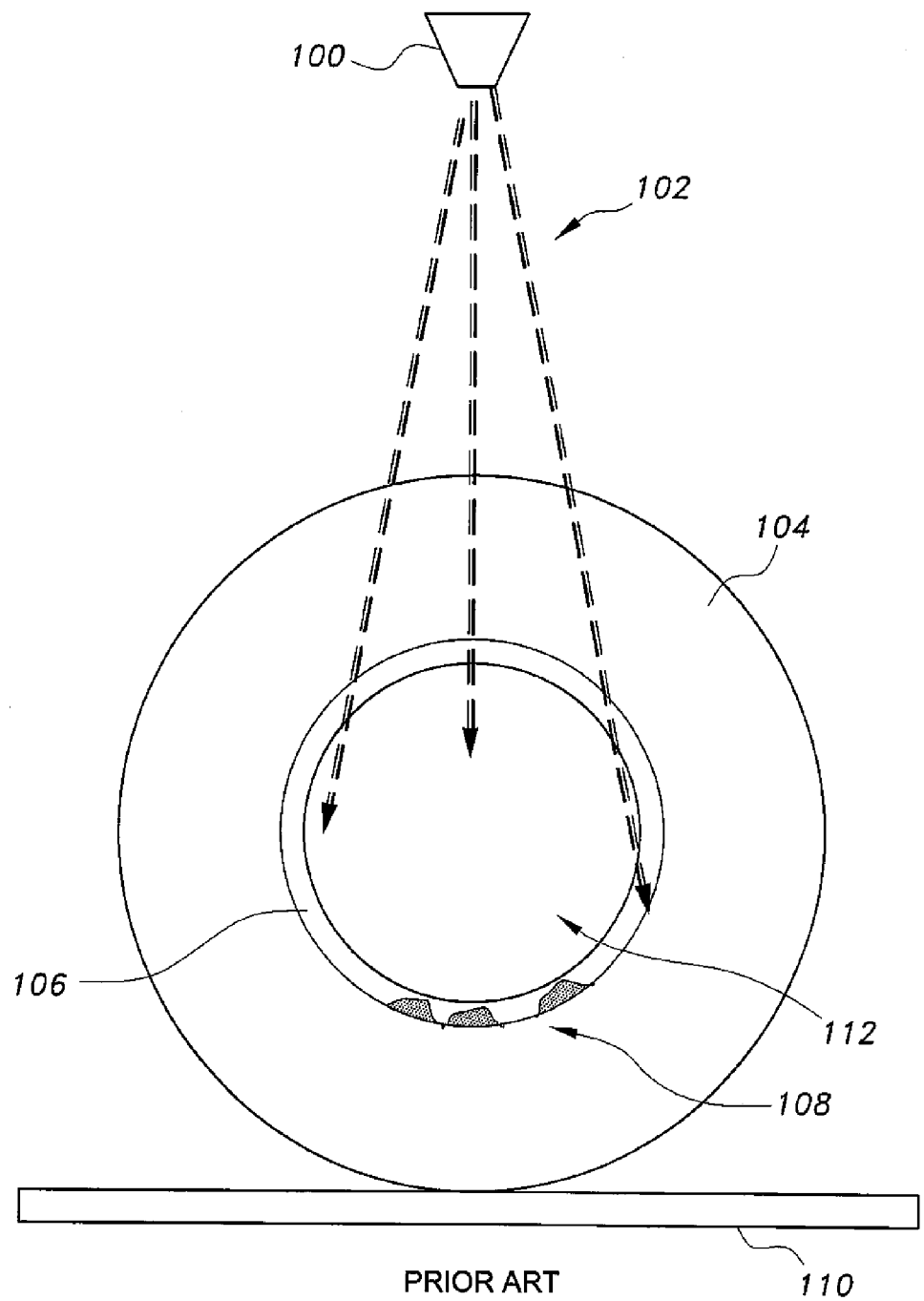
FIG. 2 is a diagram illustrating a prior art approach to direct radiographic inspection of a pipe.
Figure 3:
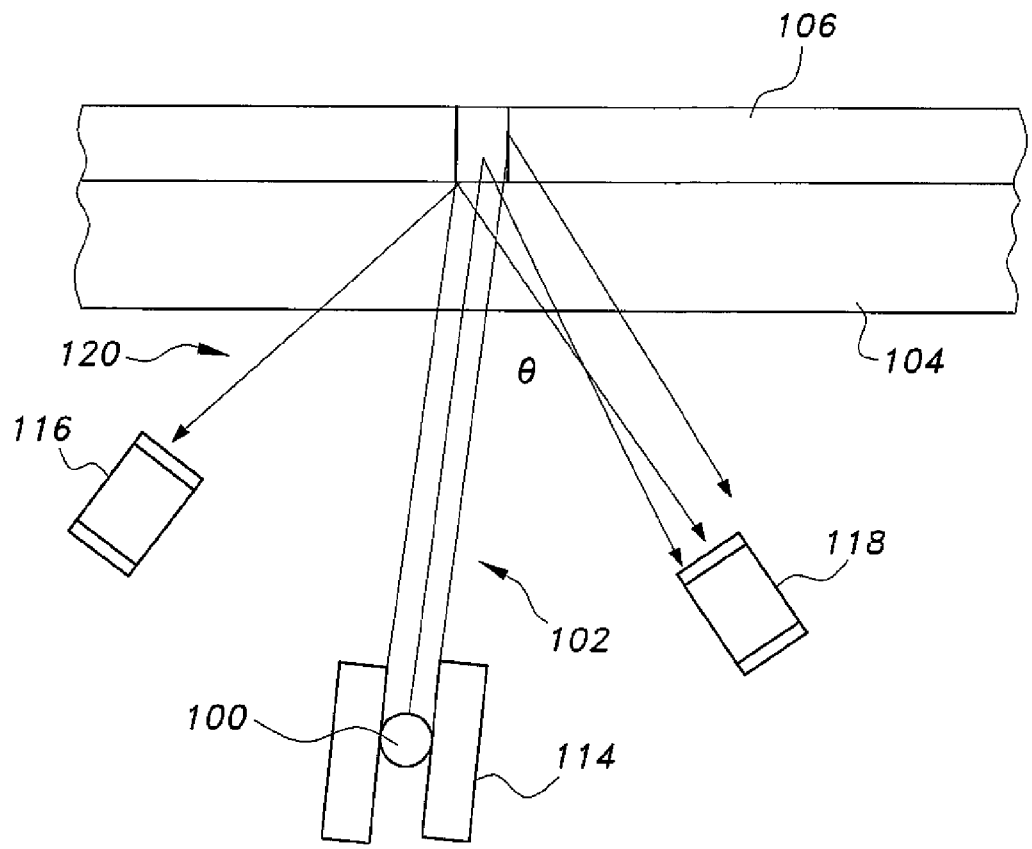
FIG. 3 is a diagram illustrating a prior art technique for inspection of an insulated pipe by backscattered radiation.

As noted above with regard to the conventional backscatter inspection system of FIG. 3, backscattered gamma radiation is not mono-directional. The backscattered rays are scattered in all directions. As shown in FIG. 1, the present collimator 10 may be positioned in front of a radiographic imaging plate 50 (or any other radiographic imaging device, such as radiographic film or the like) in order to select a parallel backscattered beam. As shown in FIG. 1, an exemplary gamma radiation source 52, which is housed within an exemplary radiation shield 54, generates gamma rays for the inspection of an insulated pipe P, similar to that described above with regard to FIGS. 2 and 3. The gamma radiation passes through the insulation layer 56, and is scattered by the metallic pipe material 58. In FIG. 1, incident gamma rays $\gamma_1$ are scattered by a non-corroded portion 60 of the pipe P, and incident gamma rays $\gamma_2$ are scattered by a corroded portion 62. The scattered rays $\gamma_3$ and $\gamma_4$ are scattered from the non-corroded portion 60 and the corroded portion 62, respectively. It should be understood that the specific application to insulated pipes is shown and described for exemplary purposes only, and that the imaging system may be used for any desired type of testing, inspecting and imaging. It should be further understood that X-rays may be used rather than gamma rays.

The collimator 10 is placed in front of the radiographic imaging plate 50 to filter backscattered rays $\gamma_3$ and $\gamma_4$ into individual parallel beams, filtering out beams that are not orthogonal to the plane of the radiographic imaging plate 50. It should be understood that the configuration of the source 52, the shield 54, the radiographic plate 50, and the pipe P are shown in FIG. 1 for exemplary and illustrative purposes only. The arrangement shown in FIG. 1 provides a thickness or density profile of the pipe wall 58, rather than a surface image.

Figure 4:
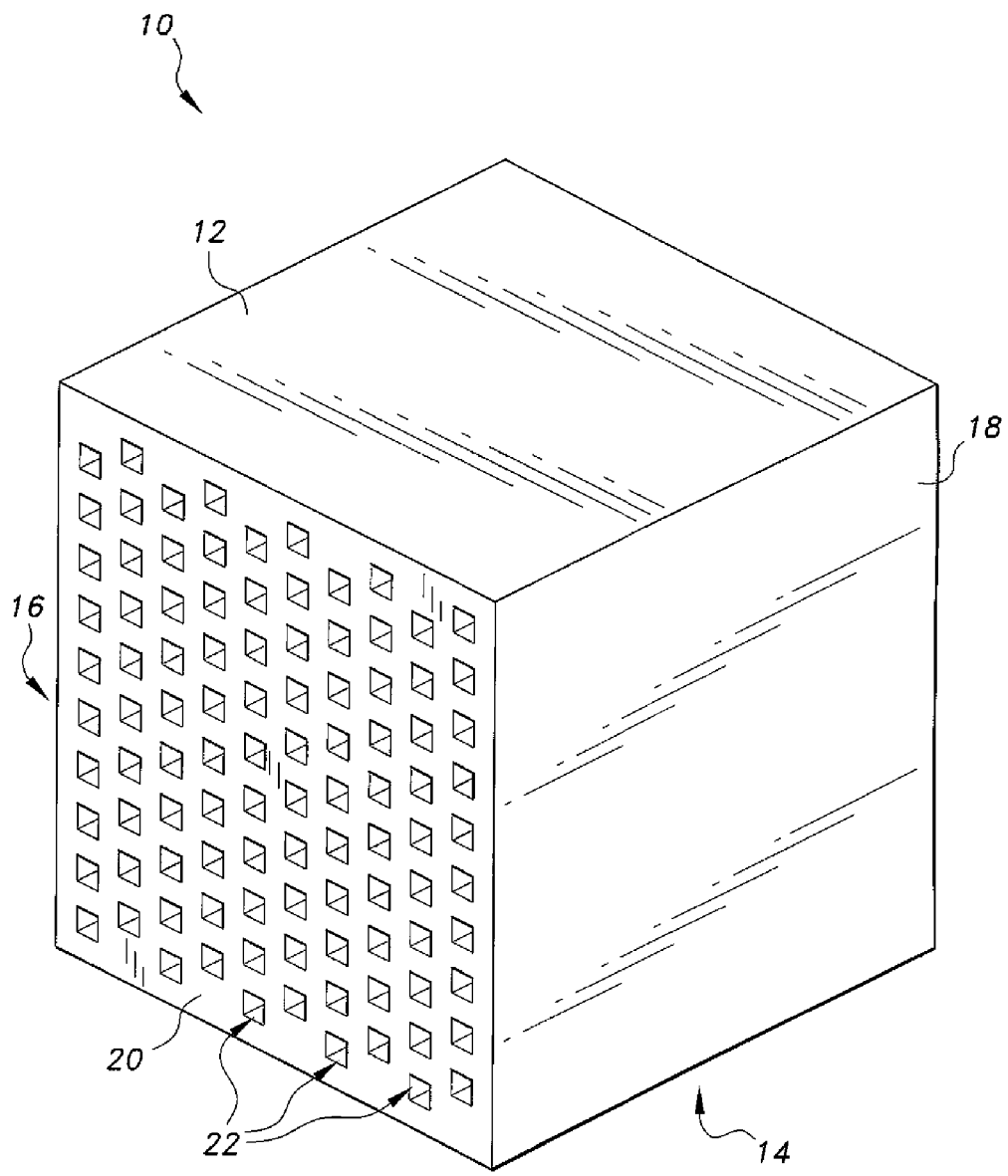
FIG. 4 is a perspective view of a first embodiment of a collimator for backscattered radiation imaging according to the present invention.

As shown in FIG. 4, the collimator 10 is preferably formed as a parallelepiped, having solid, longitudinally opposed top and bottom walls 12, 14, respectively, and solid, laterally opposed sidewalls 16, 18. A front wall 20 is transversely opposed to a rear wall (not shown), and a plurality of passages 22 pass through the collimator 10 from the front wall 20 to the rear wall along the transverse direction.

Figure 5:
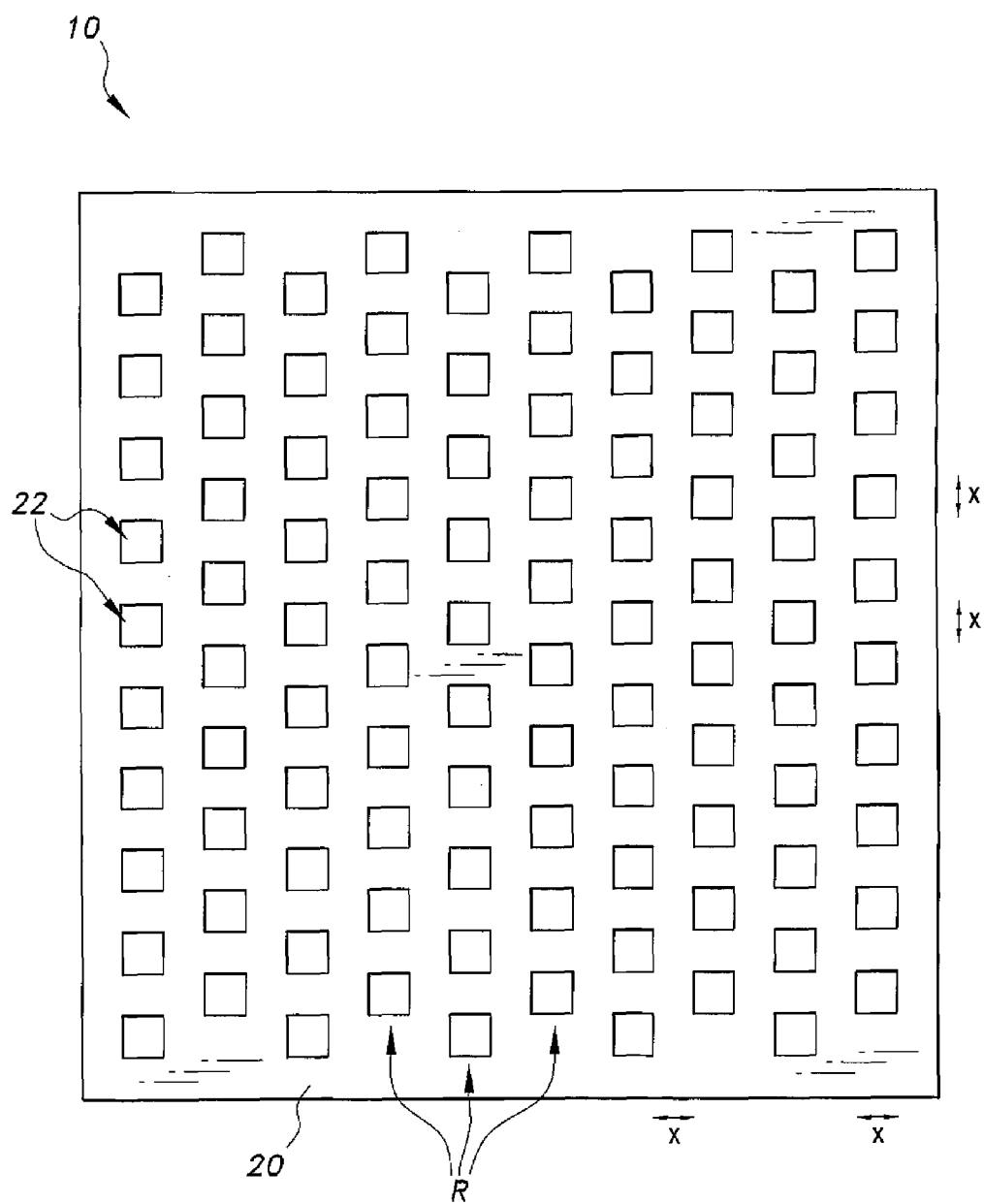
FIG. 5 is a front view of the collimator of FIG. 4.

As best shown in FIG. 5, each passage 22 preferably has a square cross-section, each side of each passage 22 having a length X. In the orientation of FIG. 5, the plurality of passages 22 are divided into vertical rows R. Each vertical row R is spaced apart from the adjacent rows R by distance X. Additionally, each passage 22 is vertically spaced apart from adjacent passages 22 by distance X. Further, as shown in FIG. 5, each vertical row is vertically staggered with respect to its adjacent rows by distance X.

In use, since the collimator 10 only selects one particular set of parallel gamma rays, the passage walls will stop a large portion of the backscattered radiation, thus producing an incomplete image on the radiographic imaging plate 50. Thus, multiple exposures are employed, and the collimator is shifted laterally by incremental steps between exposures, as indicated by the directional arrows in FIG. 1. It should be understood that the body of the collimator 10 may be formed from any suitable type of gamma radiation shielding material, as is well known in the art for radiation collimation. Further, as an alternative to the lateral shifting in incremental steps, the collimator 10 may be vibrated in an oscillatory fashion in the lateral direction.

Figure 6:
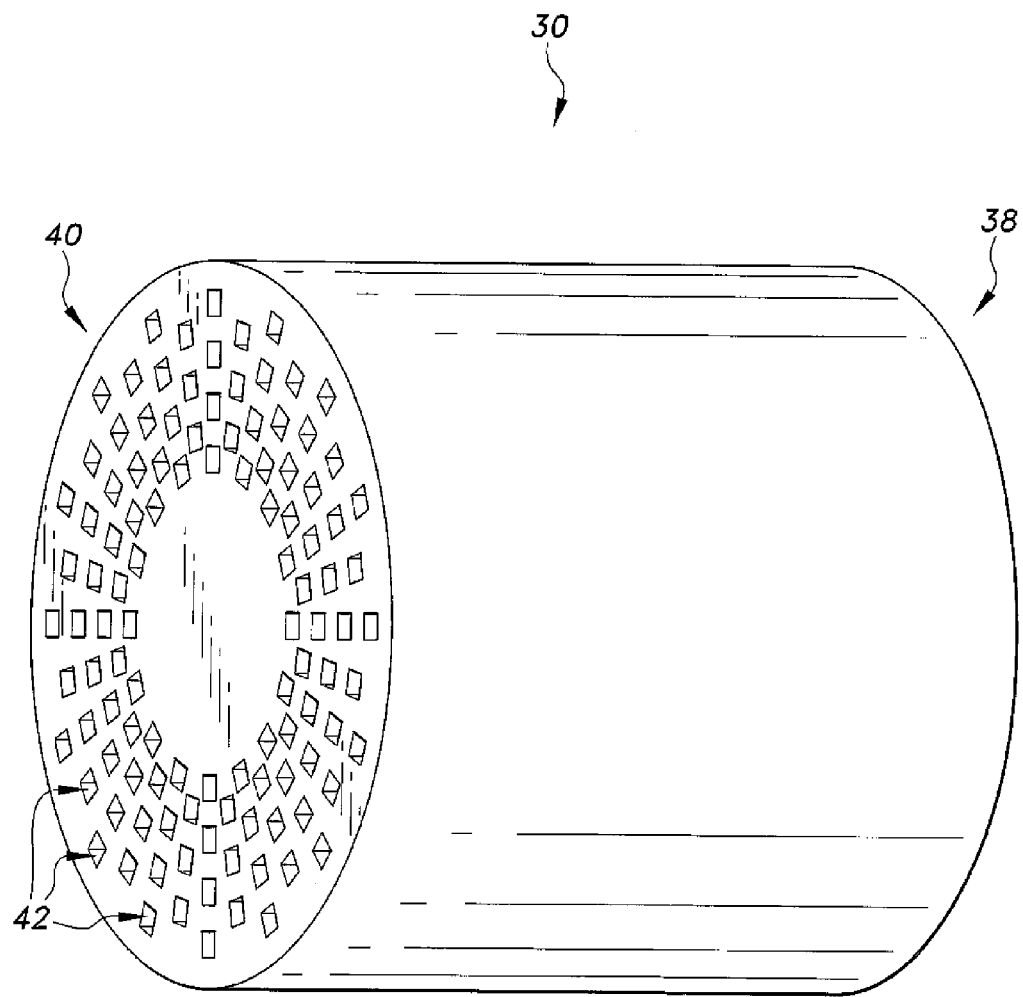
FIG. 6 is a perspective view of an alternative embodiment of a collimator for backscattered radiation imaging according to the present invention.
Figure 7:
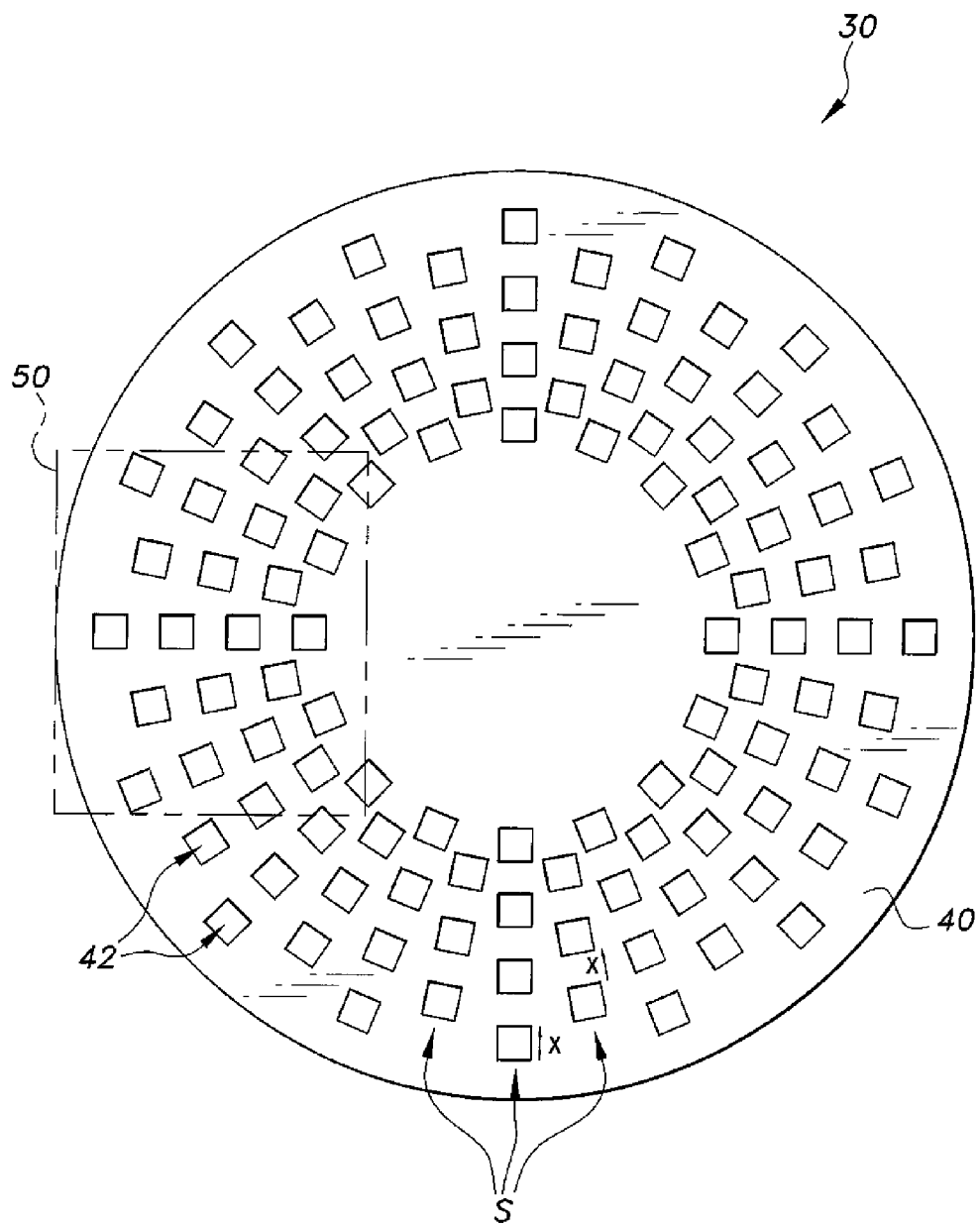
FIG. 7 is a front view of the collimator of FIG. 6.

FIGS. 6 and 7 illustrate an alternative embodiment designated as collimator 30. Rather than the parallelepiped collimator 10, collimator 30 is formed as a cylinder, having axially opposed rear and front walls 38, 40, respectively, and a solid side wall 36. Passages 42, each of which preferably has a square cross-section, extend axially through the body of the collimator 30. Similar to the vertical rows R of passages in the collimator 10, the collimator 30 has a plurality of radially extending rows S. Each passage 42 has a side length of X, and each passage 42 is radially spaced apart from the other passages 42 in the same radial row S by distance X.

In FIG. 7, the positioning of the radiographic imaging plate 50 is shown by the dashed-line image. As in the previous embodiment, in use, since the collimator 30 only selects one particular set of parallel gamma rays, the passage walls will stop a large portion of the backscattered radiation, thus producing an incomplete image on the radiographic imaging plate 50. Thus, multiple exposures are employed, and the collimator 30 is rotated by incremental steps between exposures, instead of the lateral shifting of collimator 10. It should be understood that the body of the collimator 30 may be formed from any suitable type of gamma radiation shielding material, as is well known in the art for radiation collimation. Further, as an alternative to the rotational shifting in incremental steps, the collimator 30 may be vibrated in oscillatory fashion, about its axis. It should be understood that the overall dimensions of the collimators 10 and 30 may be varied, depending upon the energy of the backscattered radiation.

It is to be understood that the present invention is not limited to the embodiments described above, but encompasses any and all embodiments within the scope of the following claims.

We claim:

1. A method of performing backscattered radiation inspection of an object to be imaged, comprising the steps of:
providing a collimator having a plurality of parallel, arrayed passages extending therethrough, wherein the collimator comprises a substantially cylindrical radiation-shielding body having a solid sidewall and axially opposed front and rear walls, wherein the plurality of parallel, arrayed passages extend axially through the radiation-shielding body, each of the plurality of parallel, arrayed passages extending between the front and rear walls and having a square cross-section;
positioning the collimator in front of a radiographic imaging device such that the plurality of parallel, arrayed passages are positioned orthogonal to a plane of the radiographic imaging device;
exposing a wall of object to be imaged to gamma radiation;
making image exposures on the radiographic imaging plate of backscattered gamma radiation from the wall of the object; and
shifting the position of the collimator between each of the exposures, wherein said shifting the position of the collimator comprises incrementally rotating the collimator about its longitudinal axis.

2. A method of performing backscattered radiation inspection of an object to be imaged, comprising the steps of:
providing a collimator having a plurality of parallel, arrayed passages extending therethrough, wherein the collimator comprises a substantially cylindrical radiation-shielding body having a solid sidewall and axially opposed front and rear walls, wherein the plurality of parallel, arrayed passages extend axially through the radiation-shielding body, each of the plurality of parallel, arrayed passages extending between the front and rear walls and having a square cross-section;
positioning the collimator in front of a radiographic imaging device such that the plurality of parallel, arrayed passages are positioned orthogonal to a plane of the radiographic imaging device;
exposing a wall of object to be imaged to gamma radiation;
making image exposures on the radiographic imaging plate of backscattered gamma radiation from the wall of the object; and
shifting the position of the collimator between each of the exposures, wherein said shifting the position of the collimator comprises rotational oscillation of the collimator about its longitudinal axis.

* * * * *